United States Patent [19]

May

[11] 4,084,280
[45] Apr. 18, 1978

[54] TOOTH BRUSH

[76] Inventor: Bob May, P.O. Box 212, River Forest, Ill. 60305

[21] Appl. No.: 772,304

[22] Filed: Feb. 25, 1977

[51] Int. Cl.² .......................................... A46B 13/02
[52] U.S. Cl. .................................... 15/22 R; 74/22 R
[58] Field of Search ................ 15/22 R, 22 A, 22 C, 15/23, 24, 28, 29, 97 R; 51/34 K; 74/22 R; 310/80

[56] References Cited

U.S. PATENT DOCUMENTS

| 1,795,098 | 3/1931 | Scadding | 15/22 R |
| 1,945,616 | 2/1934 | Mastrud | 15/22 R X |
| 3,270,360 | 9/1966 | Kropp | 15/22 R |
| 3,661,018 | 5/1972 | Keefer et al. | 15/22 R |

FOREIGN PATENT DOCUMENTS 366,472  2/1963  Switzerland ............................ 15/23

Primary Examiner—Edward L. Roberts
Attorney, Agent, or Firm—Paul H. Gallagher

[57] ABSTRACT

A power tooth brush, including a barrel or casing with an electric motor therein. A rotating brush member has a shank fitted in the front end of the barrel with a brush element exposed to the exterior. Sleeve means drivingly interconnects the shank of the brush member and the drive shaft of the motor. The sleeve is of compound construction, including a fixed element and a movable element, with cam means interacting between the elements producing axial vibration of the brush member in response to its rotation. In one form, a battery is included for running the motor, so that the device is self-contained and in this form it is adapted for having a cap fitted thereon, whereby it is easily carried in the pocket and easily used in travel. Another form is adapted to plug-in operation.

1 Claim, 8 Drawing Figures

U.S. Patent April 18, 1978 4,084,280
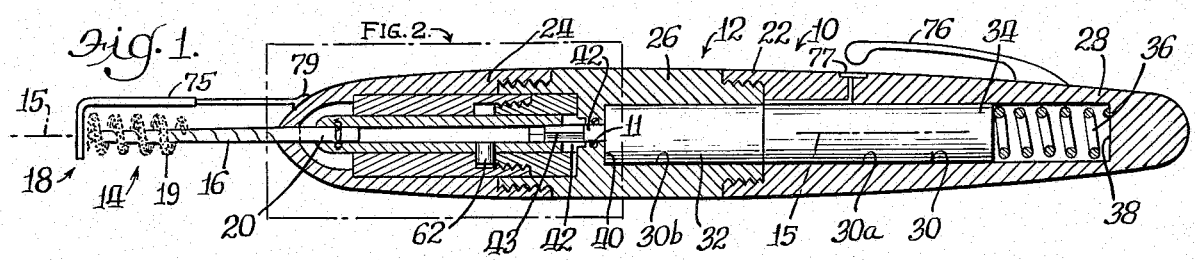
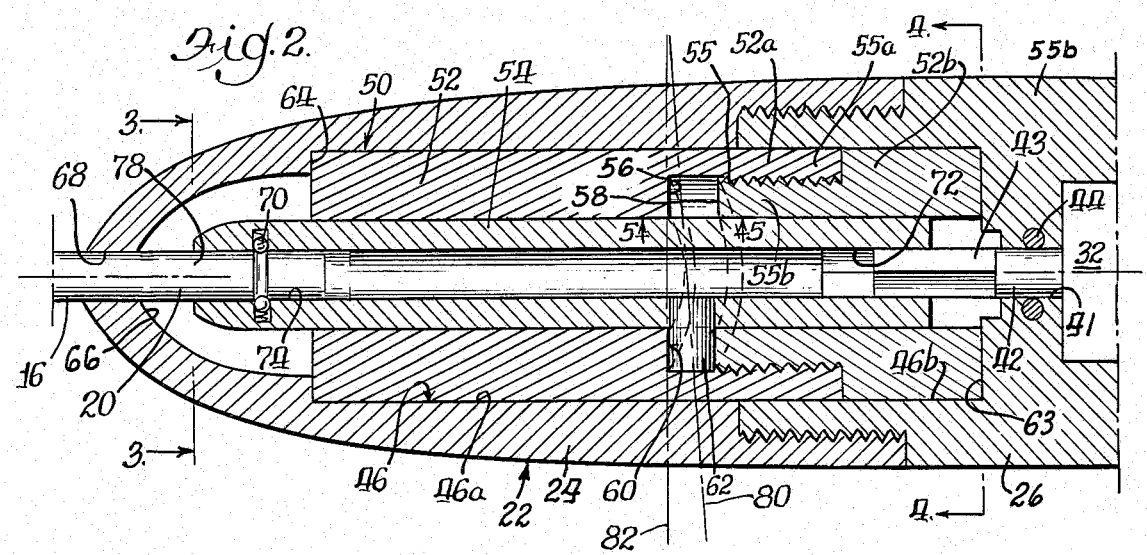
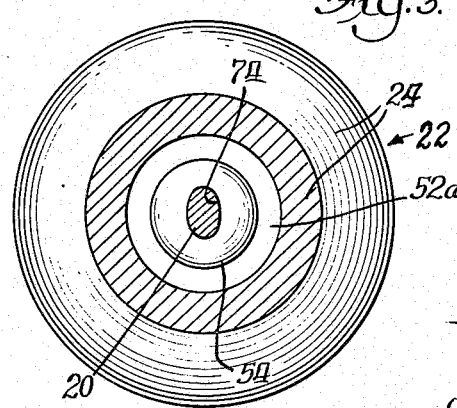
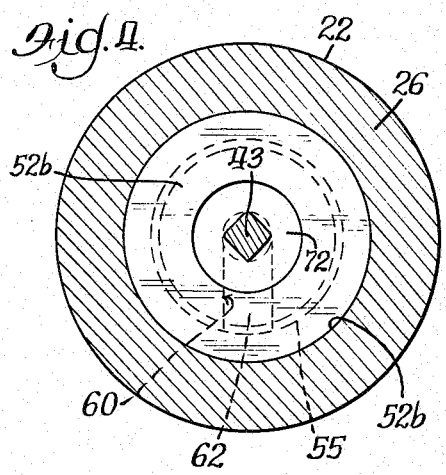
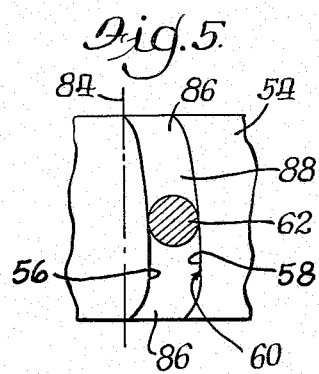
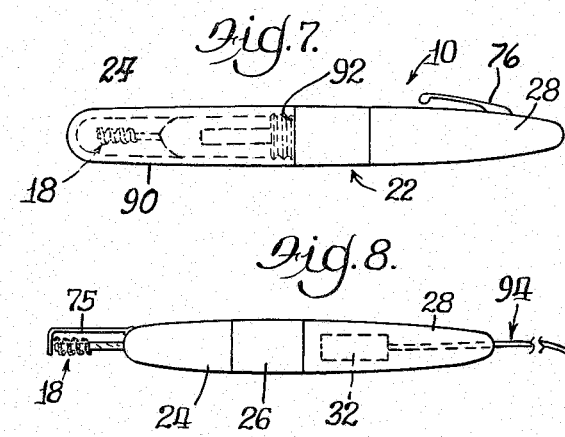
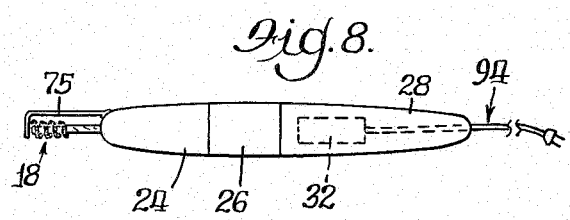

TOOTH BRUSH

FIELD OF THE INVENTION

The invention resides in the general field of power tooth brushes, and particularly for personal use, as distinguished from professional use as by a dentist.

OBJECTS OF THE INVENTION

A broad object of the invention is to provide a power tooth brush which is effective for producing a cleaning function, when used by an individual, that highly simulates the cleaning action by a dentist, and that is unusually effective for causing the bristles to readily enter into the spaces between the teeth.

A more specific object is to provide a power tooth brush of the foregoing general character, having a rotating brush member which is also vibrated axially in response to this rotation, whereby to enhance the function of entering into the spaces between the teeth.

Another object is to provide a power tooth brush of the foregoing character, having an unusually compact arrangement with a simple construction of brush member detachably mounted in the main parts of the toothbrush and easily removed therefrom, and with effective sealing means in the face of the detachable mounting of the brush member.

An additional object is to provide a power tooth brush of the foregoing character which is of unusually compact design so that it can be easily and conveniently carried in the pocket.

DESCRIPTION OF A PREFERRED EMBODIMENT

In the drawings:

FIG. 1 is an axial sectional view of the power tooth brush made according to the present invention;

FIG. 2 is a sectional view on an enlarged scale of that portion of FIG. 1 enclosed in the dot-dash rectangle 2;

FIG. 3 is a sectional view taken at line 3—3 of FIG. 2;

FIG. 4 is a sectional view taken at line 4—4 of FIG. 2;

FIG. 5 is a developed view as indicated at line 5—5 of FIG. 2 showing the interior surface of the inner-sleeve;

FIG. 6 is a diagrammatic view of a series of teeth and the brush element of the invention applied thereto;

FIG. 7 is a small scale exterior view, devoid of details, showing the tooth brush of the invention having a cap applied thereto; and FIG. 8 is a small scale exterior view showing a form adapted to plug-in operation of the electric motor.

Referring in detail to the accompanying drawings and first of FIG. 1, the tooth brush as a whole is indicated at 10 and includes a main part or body 12 and a brush member 14 detachably mounted therein. The tooth brush has a main centra longitudinal axis 15.

The brush member 14 has a shank 16 and a brush element 18 including radial bristles. The brush element in the main may be of known construction, such for example as one having the bristles 19 secured in a twisted shank, although the shank at its rear end has a portion 20 of non-circular, such as oval, shape as shown particularly in FIG. 3. The bristles 18 are distributed entirely circumferentially around the shank.

The body 12 includes a barrel 22, made up of three sections, a front section 24, a middle section 26 and a rear section 28, the adjacent sections being secured together as by threading as shown. The junction surfaces may be provided with a cement, which is insoluble in water or toothpaste or toothpowder solutions, for normally securing the sections together in semi-permanent condition, although these sections may be separated and reconnected by a service or repair man. The purpose of the cement is to seal the interior from moisture in the normal use of the device, although the sections can be separated for servicing purposes.

The barrel is provided with a rear main bore 30 made up of two portions, 30a, 30b which are aligned when the sections 26, 28 are secured together. Mounted in the bore 30 is an electric motor 32 and spring 36 confined between the battery 34 and the rear-end surface 38 of the bore. The spring biases the battery into engagement with the motor and the motor into engagement with an annular front end surface 40 surrounding a reduced bore 41 communicating with the bore 30.

The motor 32 has a forwardly extending rotating drive shaft 42 with an outer end element 43 of non-circular, such as square, shape, as shown particularly in FIG. 4. The drive shaft extends through the reduced bore 41, and the rear portion 42 of the shaft is cylindrical and engaged by an "O" ring 44, sealing the rear main bore 30.

The barrel 22 is also provided with a front main bore 46 adjacent its front end, being made up of bore portions 46a, 46b, aligned when the respective barrel sections 24, 26 are secured together. This bore communicates with the bore 41.

Mounted in the bore 46 is what is termed a drive unit 50 and includes an outer sleeve 52 and an inner sleeve 54. The outer sleeve 52 is made up of axially aligned front and rear sections 52a, 52b connected together at 55 by means of an outer tubular flange 55a on the front section 52a, and an inner boss 55b on the rear section 52b. The radially inner portions of the sleeve sections have interfacing end surfaces 56, 58 which are spaced apart when these sections are secured together, and together forming a cam track identified at 60, which is circumferentially continuous, and receives a pin 62 mounted in the inner sleeve 54 which acts as a cam follower therein. The specific shape of the cam track and its function with the pin 62 will be referred to in detail hereinbelow.

The front main bore 46 is provided with an annular rear end surface or shoulder 63 surrounding the reduced bore 41, which is engaged by the outer sleeve 52. The bore 46 is also provided with a front end annular surface or shoulder 64 engaged by the front end of the outer sleeve 52, and forwardly of the surface 64 is a further annular shoulder 66 surrounding a reduced bore or aperture 68, opening forwardly and receiving the shank 16 of the brush member. The outer sleeve 52 is normally in fixed position, and a cement may be utilized in the manufacture of the device or in the servicing of it, to aid in stationarily positioning it, and to provide a sealing effect.

The inner sleeve 54 is freely rotatable in the outer sleeve, and its inner surface has at least a portion 72 at its rear end complementary in cross sectional shape to the end elements 43 of the drive shaft 42 of the motor for rotational driving connection therebetween. The drive shaft element has an axially slidable fit in the sleeve. Similarly the sleeve at its front end has a portion 74 of non-circular cross-sectional shape complementary to the end portion 20 of the brush shank. The intermediate portion of the inner surface of the sleeve may be cylindrical to simplify its manufacture.

The sleeves 52, 54 are easily placeable in the bore 46 upon separation of the barrel section 24, 26, and the drive shaft 44 of the motor is easily insertable into the inner sleeve 54 when the motor is put in place in the rear main bore 30 upon separation of the barrel section 26, 28. Similarly the rear end of the brush shank 16 is easily insertable into the inner sleeve by merely inserting it through the aperture 68 and by continuation of that movement into the inner sleeve. Preferably the inner extension 20 of the brush shank is of reduced dimension relative to the remainder of the brush shank to form a shoulder 78 which engages the sleeve and thus limits the movement in that direction of the brush member.

As stated above, the snak of the brush member is normally retained in the inner sleeve by friction. This retention is aided by an "O" ring 70 fitted in a groove in the inner surface of the sleeve and gripping the shank. The brush member is carried by the inner sleeve in the axial vibration.

A shield 75 is secured to the barrel at 79, as by welding or by screws, for protection of the inner surface of the cheek the shield preferably being arcuate and partially surrounding the brush element.

The barrel may be provided with a pocket clip 76, and this clip may be utilized as a manually actuarted switch element, engageable with a contact 77 for energizing the motor.

The cam track 60 has an axial component, i.e., it does not lie in a perpendicular plane. FIG. 5 is a developed view of the inner surface of the outer sleeve 52 as indicated at line 5—5 of the inner surface of the inner sleeve. The cam track is positioned at an angle to the perpendicular, as indicated by the dot-dash line 80 (FIG. 2), the dot-dash line 82 indicating the perpendicular. In FIG. 5, the dot-dash line 84 is perpendicular, being touched by the end portions 86 of the cam track which represent one position circumferentially of the cam track, and the central portion 88 which represents the diametrically opposite position, is spaced from that line.

Upon rotation of the inner sleeve 54, by the motor, the cam follower pin 62 in riding in the cam track causes axial vibration of the inner sleeve 54, the pin being fixed in the inner sleeve as noted, and in following the non-perpendicular shape of the cam track, the sleeve is accordingly vibrated axially. Since the brush member 14 is normally fixed with the inner sleeve, it vibrates therewith, and thus the brush member follows both a rotating and axially vibrating action.

The rotation of the brush is of course beneficial, as always recommended by dentists, rather than in a reciprocating direction across the teeth, so as to facilitate the penetration of the bristles into the spaces between the teeth. This penetraton of the bristles is greatly aided and facilitated by the axial vibrating action, that is, while the bristles are moving in rotating direction, they follow the general direction of the spaces between the teeth, but they penetrate more readily if they are also vibrated axially. FIG. 6 shows a line of contiguous teeth 90 with the spaces 92 indicated therebetween, and the position of the bristles in entering into the spaces between the teeth. FIG. 6 is a view in the direction of the axes of the teeth and the outer elevational view of the brush. FIG. 6 shows the axis 15 about which the brush rotates, and includes a double-headed arrow 94 indicating the axial vibration of the brush in both of opposite directions.

The extent of the axial vibration of the brush need not be great, and in fact may be very minor such as on the order of about 1/32 of an inch; in this regard the representations in FIG. 2 and 5 are exaggerated in showing the extent of such axial vibrations. The axial vibration of the brush, even being of such a minor extent, nevertheless greatly aids the bristles in penetrating into the spaces between teeth.

FIG. 7 shows the tooth brush as having a cap 90 fitted over the otherwise exposed brush member 18, being fitted on the barrel 22 in a suitable and known manner which normally frictionally retains it there, the barrel having a shoulder 92 for limiting the extent of movement of the cap in fitting it in position. Thus the device as shown in FIG. 7 can conveniently be carried in the pocket or in the purse for use at places away from home.

FIG. 8 shows a tooth brush made according to the present invention which utilizes a plug-in arrangement as indicated at 94 for driving the motor 32, instead of providing a battery such as 34, which may be convenient in eliminating the need for supplying new batteries periodically.

I claim:

1. A tooth brush of the character disclosed, comprising, a barrel having a rear end and a front end and made up of three sections, a middle section, a front section and a rear section, the sections being normally connected together for use of the device, but being separable, the middle section and the rear section having bore portions which are axially algined when those sections are fitted together, and which form a rear main bore, the middle section and the front section having bore portions which are aligned when those sections are fitted together and which form a front main bore, the middle section having a reduced bore interconnecting the rear main bore and front main bore, and the middle section having a rearwardly facing annular shoulder surrounding the reduced bore and forming the front end surface of the rear main bore and also having a forwardly facing annular shoulder surrounding the reduced bore and forming the rear end surface of the front main bore, the front section having an aperture at its front end leading from the front main bore to the exterior, a motor in the rear main bore having a drive shaft extending through the reduced bore into the front main bore, a battery in the rear main bore in operative engagement with the motor, a spring in the rear main bore biasing the battery into engagement with the motor and the motor into engagement with said front end surface of the bore, the rear barrel section having contacts for establishing an electrical circuit through the motor and battery, and also having a pocket clip normally in an inactive position, but movable by the hand into engagement with the motor contacts for completing an electrical circuit through the battery and motor, a drive unit in the front main bore including an outer sleeve made up of relatively longitudinally positioned sections normally fitted together in the assembled device, and the sleeve being confined in the front main bore between said front annular shoulder and a surface of the front section adjacent the front end of the latter, the sections of the outer sleeve having interfacing end surfaces spaced apart when they are assembled and defining therebetween an annular cam track disposed at an acute angle to the main longitudinal axis of the device, the drive unit also including an inner sleeve rotationally and reciprocally disposed in the outer sleeve and having an element at its rear end in drive transmitting connection with the shaft of the motor, said inner sleeve having a radial pin extending into said cam track, the tooth brush also including a brush member having a brush element on the exterior of the barrel an a shank extending through the front end aperture of the barrel into the front end of the inner sleeve of the drive unit, and normally frictionally held in and carried by that inner sleeve, but detachable therefrom through the front end of the barrel, the inner sleeve, in response to rotation by said motor, following a reciprocatory movement by the interconnection between said pin and cam track for reciprocating the sleeve and thereby reciprocating the brush member.

* * * * *